Figure 1:
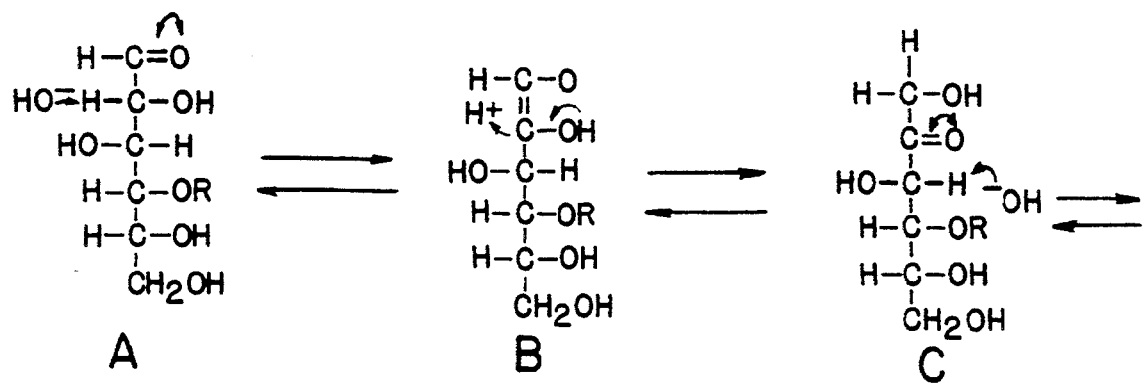
Figure 1:
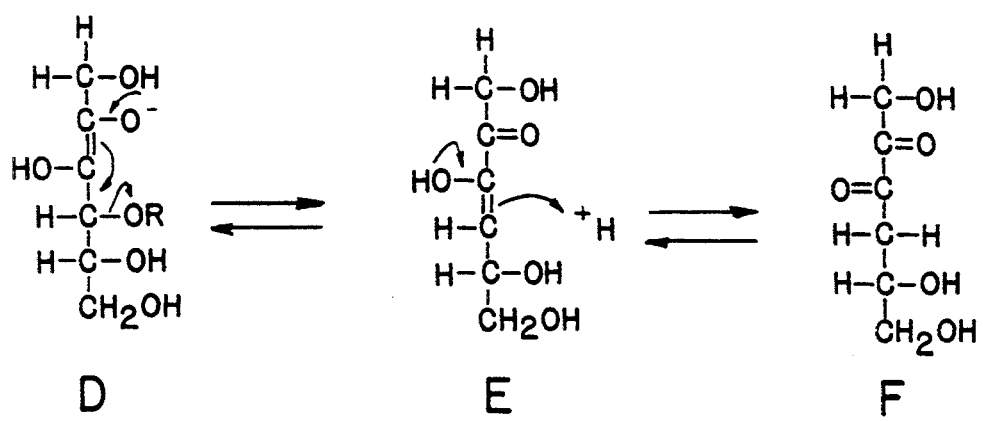
Figure 1:
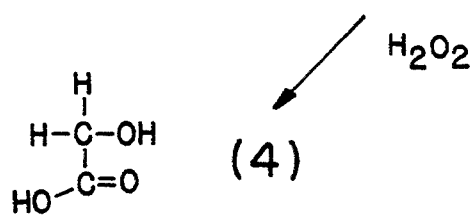
Figure 1:
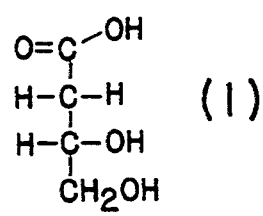

United States Patent [19]

Hollingsworth

[11] Patent Number: 5,374,773
[45] Date of Patent: Dec. 20, 1994

[54] PROCESS FOR THE PREPARATION OF 3,4-DIHYDROXYBUTANOIC ACID AND SALTS THEREOF

[75] Inventor: Rawle I. Hollingsworth, Haslett, Mich.

[73] Assignee: Board of Trustees operating Michigan State University, East Lansing, Mich.

[21] Appl. No.: 141,635

[22] Filed: Oct. 27, 1993

Related U.S. Application Data

[62] Division of Ser. No. 966,411, Oct. 26, 1992, Pat. No. 5,319,110, which is a division of Ser. No. 698,854, May 13, 1991, abandoned.

[51] Int. Cl.$^5$ .......................................... C07C 51/285
[52] U.S. Cl. .................... 562/515; 562/579; 562/587
[58] Field of Search ................ 562/587, 515, 579

[56] References Cited

U.S. PATENT DOCUMENTS 3,631,189  12/1971  Snapp et al. .................... 260/429 R

FOREIGN PATENT DOCUMENTS 0513430  11/1992  European Pat. Off. .

OTHER PUBLICATIONS

Corbett, W. M., et al., J. Chem. Soc. 1431–1435 (1955).
Green, J. W., J. Amer. Chem. Soc. 78:1894–1897 (1956).
Rowell, R. M., et al., Carbohydr. Res. 11:17–25 (1969).
Isbell, H. S., J. Res. Natl. Bur. Stand., 29:227 (1942).
Moody, G. J., Advances in Carbohydr. Chem., 19:149–179 (1964).
Glattfield, J. W. E., et al., J. Amer. Chem. Soc. 40:973–992 (1918).
Nakamura, N., et al., Tetrahedron Letters, 30:2245–2246 (1989).
Zhou, B., et al., J. Amer. Chem. Soc. 105:5925–5926 (1983).
Nakamura, N., et al., Tetrahedron Letters, 31:267–270 (1990).
Isbell, H. S. et al., Carbohydrate Research, 36 C1–C4 (1974).
Isbell, H. S. et al., Carbohydrate Research, 36, 283–291 (1974).
Kirk–Othmer (3rd Edition) vol. 3, p. 944 (1978).

*Primary Examiner*—José G. Dees
*Assistant Examiner*—Barbara S. Frazier
*Attorney, Agent, or Firm*—Ian C. McLeod

[57] ABSTRACT

A process for the preparation of 3,4-dihydroxybutanoic acid (1) and salts thereof from a glucose source containing 1,4-linked glucose as a substituent is described. The process uses an alkali metal hdyroxide and hydrogen peroxide to convert the glucose source to (1). The compound (1) is useful as a chemical intermediate to naturally occurring fatty acids and is used to prepare 3,4-dihydroxybutanoic acid-gamma-lactone (2) and furanone (3), particularly stereoisomers of these compounds.

14 Claims, 6 Drawing Sheets

PROCESS FOR THE PREPARATION OF 3,4-DIHYDROXYBUTANOIC ACID AND SALTS THEREOF

This is a divisional of copending application(s) Ser. No. 08/966,411 filed Oct. 26, 1992, now U.S. Pat. No. 5,319,110, which is a divisional of Ser. No. 07/698,854, filed May 13, 1991, now abandoned.

BACKGROUND OF THE INVENTION

1. Field of the Invention

The present invention relates to a process for preparation of 3,4-dihydroxybutanoic acid and salts thereof from a D-hexose source, particularly a glucose source containing glucose as a substituent. In particular, the present invention relates to a process for preparing (S)-3,4-dihydroxybutanoic acid and salts thereof.

2. Prior Art

During the course of the development by syntheses for naturally-occurring (R)-3-hydroxy long chain fatty acids, various synthetic routes to (S)-4-bromo-3-hydroxybutanoic acid methyl or ethyl esters were examined. The general approach was to carve out this chiral fragment from a suitably modified carbohydrate structure. Initial attempts involved selective protection and structural modification of methyl alpha-D-glucopyranoside followed by cleavage to yield a 4-carbon fragment containing the required functionalities. Although this approach proved to be quite viable, it proved not to be as direct as we had envisioned.

A reaction in which some of the desired product is generated in a fewer steps from inexpensive starting materials was considered. The treatment of cellobiose, a beta-1,4-linked glucose disaccharide, maltose (the alpha-1,4-linked isomer) and other related compounds with alkali has been shown to generate low yields of the desired material along with D,L-2,4-dihydroxybutanoic acid, glycolic acid, isosaccharinic acids, ketones, diketones, glyceric acids and a myriad of other degradation and condensation products (Corbett, W. M., et al., J. Chem. Soc., 1431–1435 (1955); Green, J. W., J. Amer. Chem. Soc. 78:1894–1897 (1956); and Rowell, R. M., et al., Carbohydr. Res., 11:17–25 (1969)). Starch and cellulose also yield similar compounds in what is known as the "peeling reaction". This process is, generally, thought to have no synthetic potential. Most of the products formed in these reactions are formed from the intermediate dicarbonyl (diulose) compound F shown in FIG. 1 according to a mechanism proposed by Isbell (Isbell, H. S., J. Res. Natl. Bur. Stand., 29:227 (1942)). The dicarbonyl compound F is rapidly attacked by alkali to yield a tarry mixture and the formation of 3,4-dihydroxybutanoic acid (1) and glycolic acid (4) as shown in FIG. 1 in low yields and is slow and oxygen-dependent.

Alkaline hydrogen peroxide rapidly cleaves diketones to give carboxylic acids and treatment of diuloses and other carbohydrates with hydrogen peroxide in this manner has been described (Moody, G. J., Advances in Carbohydr. Chem., 19:149–180 (1964)). The reference does not describe the use of hydrogen peroxide to cleave a glucose source containing a 1,4-glucose linkage. Earlier work on the oxidation of maltose (Glattfeld, J. W. E., et al., J. Amer. Chem. Soc. 40:973 (1918) using base and hydrogen peroxide yielded no 3,4-dihydroxybutanoic acid but gave glycollic acid, arabonic acid, D-erythronic acid, oxalic acid and formic acid. In this work, the reaction was conducted for a very prolonged period (13 days) at room temperature followed by an undefined period at 50° C. The molar proportions of base and hydrogen peroxide were both 8 to 9 fold of the sugar proportion. These conditions cause complete conversion of product to formic acid.

3,4-Dihydroxybutanoic is a valuable chiral building block and the general strategies for obtaining it and its derivatives hinge upon the development of enzymatic systems utilizing beta-ketoesters as substrates (Nakamura, N., et al., Tetrahedron Letters, 30:2245–2246 (1989); Zhou, B., et al., J. Amer. Chem. Soc., 105:5925–5926 (1983); and Nakamura, N., et al., Tetrahedron Letters, 31:267–270 (1990)).

OBJECTS

It is therefore an object of the present invention to provide a process for preparing a 3,4-dihydroxybutanoic acid from a D-hexose source. It further an object of the present invention to provide a process which is simple, economical and inexpensive. These and other objects will become increasingly apparent by reference to the following description and the drawings.

IN THE DRAWINGS

FIG. 1 shows the mechanism of alkaline peroxide degradation of a 4-linked glucose.

Figure 2:
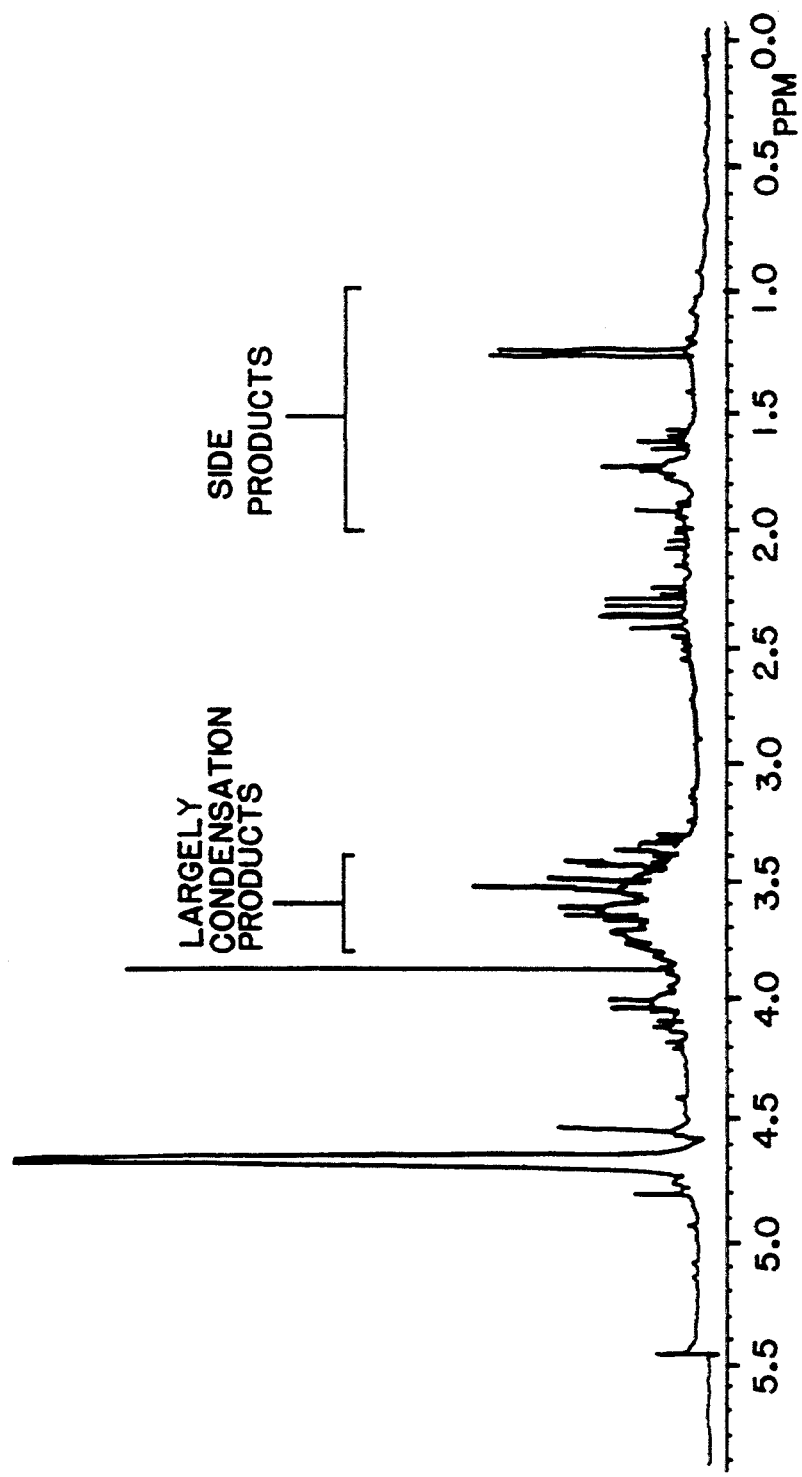

FIG. 2 shows 300 MHz $^1$H-NMR spectrum of a crude reaction mixture after treatment of maltose with 0.16M sodium hydroxide at 70° C. for 24 hours.

Figure 3:
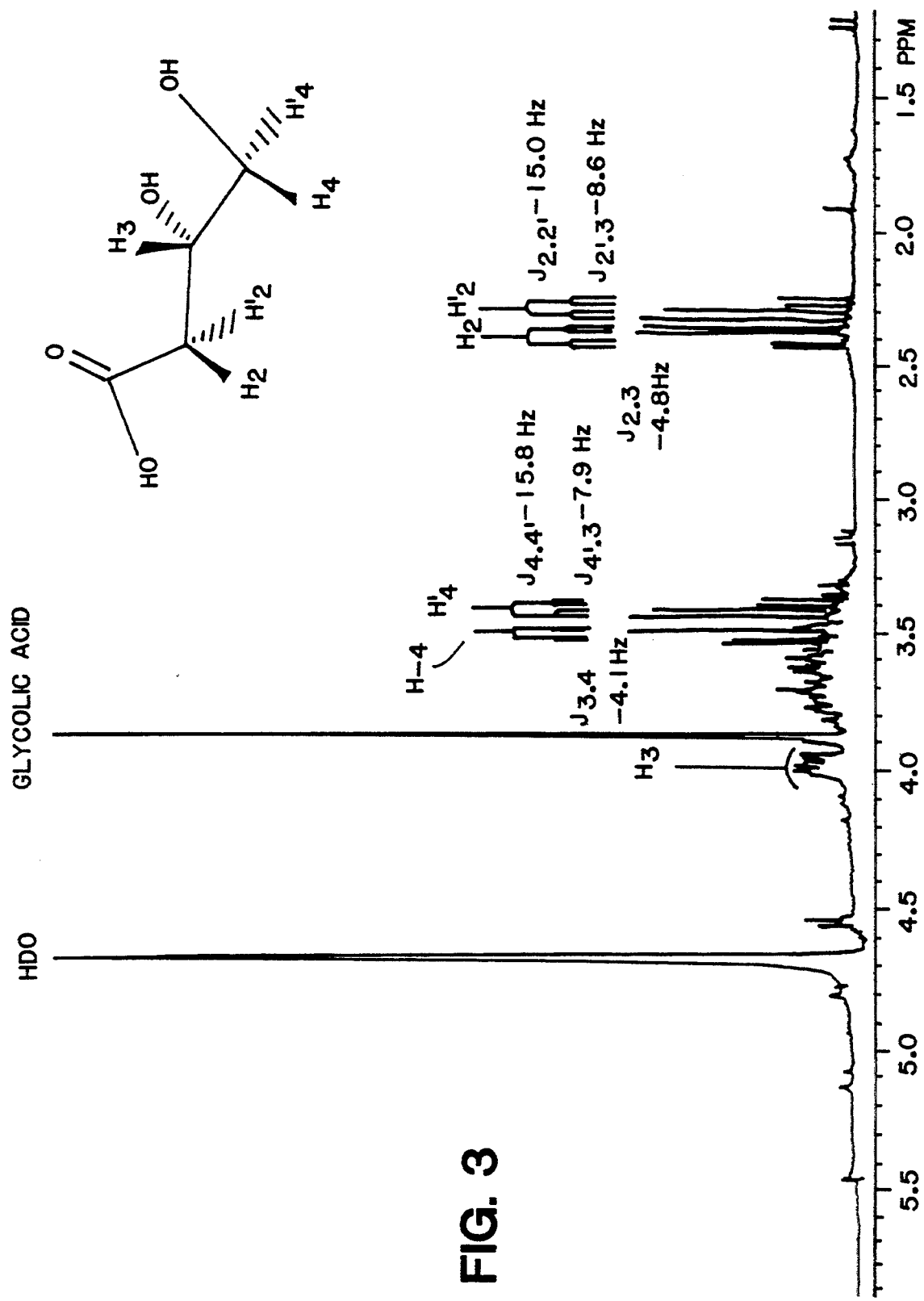

FIG. 3 shows 300 MHz $^1$H-NMR spectrum of a crude reaction mixture after treatment of maltose with 0.16M sodium hydroxide and 1.3 equivalents of hydrogen peroxide for 24 hours at 70° C.

Figure 4:
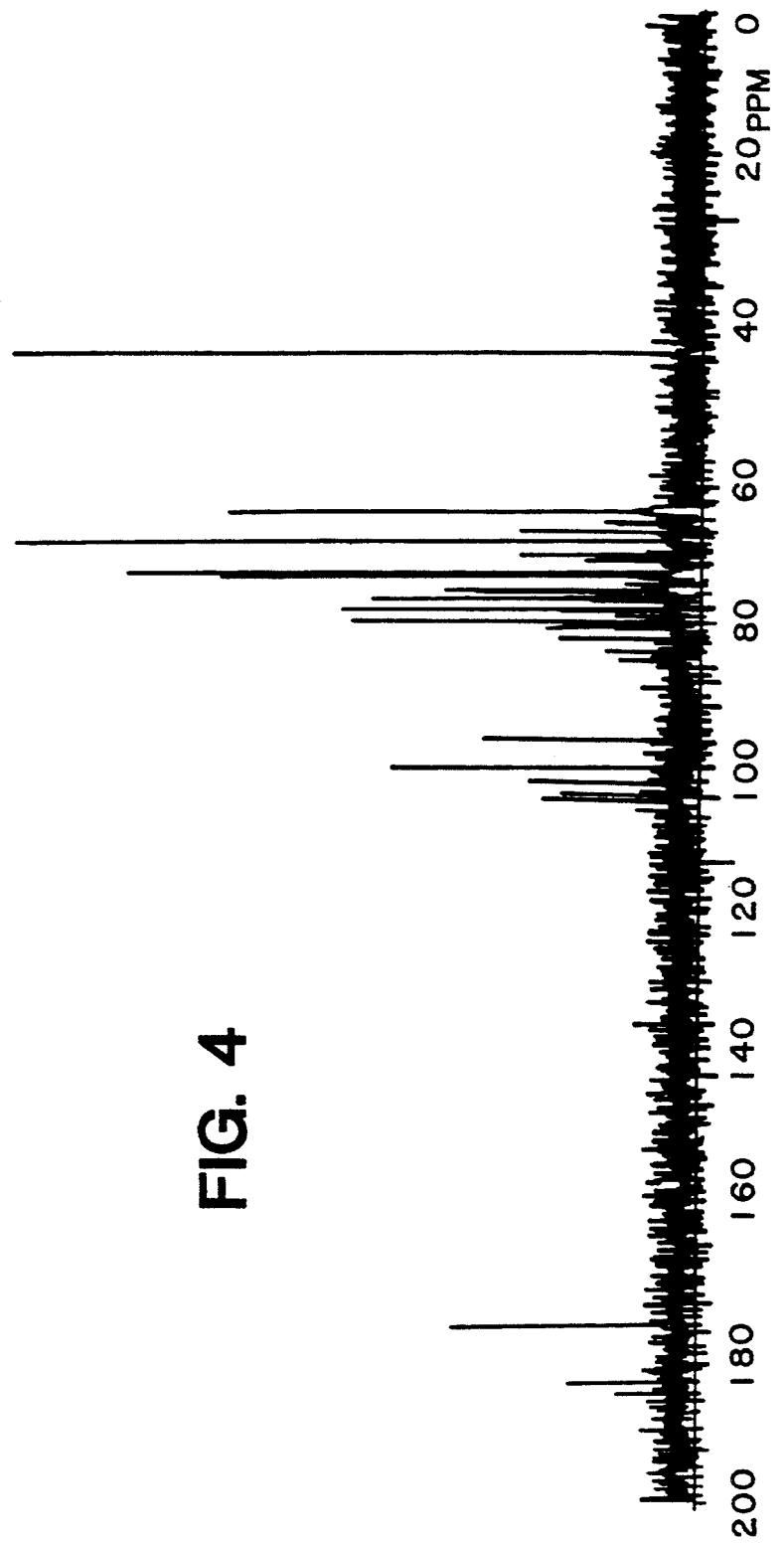

FIG. 4 shows $^{13}$C-NMR spectrum of a crude reaction mixture after treatment of maltose with 0.16M sodium hydroxide and 1.3 equivalents of hydrogen peroxide for 24 hours at 70° C.

Figure 5:
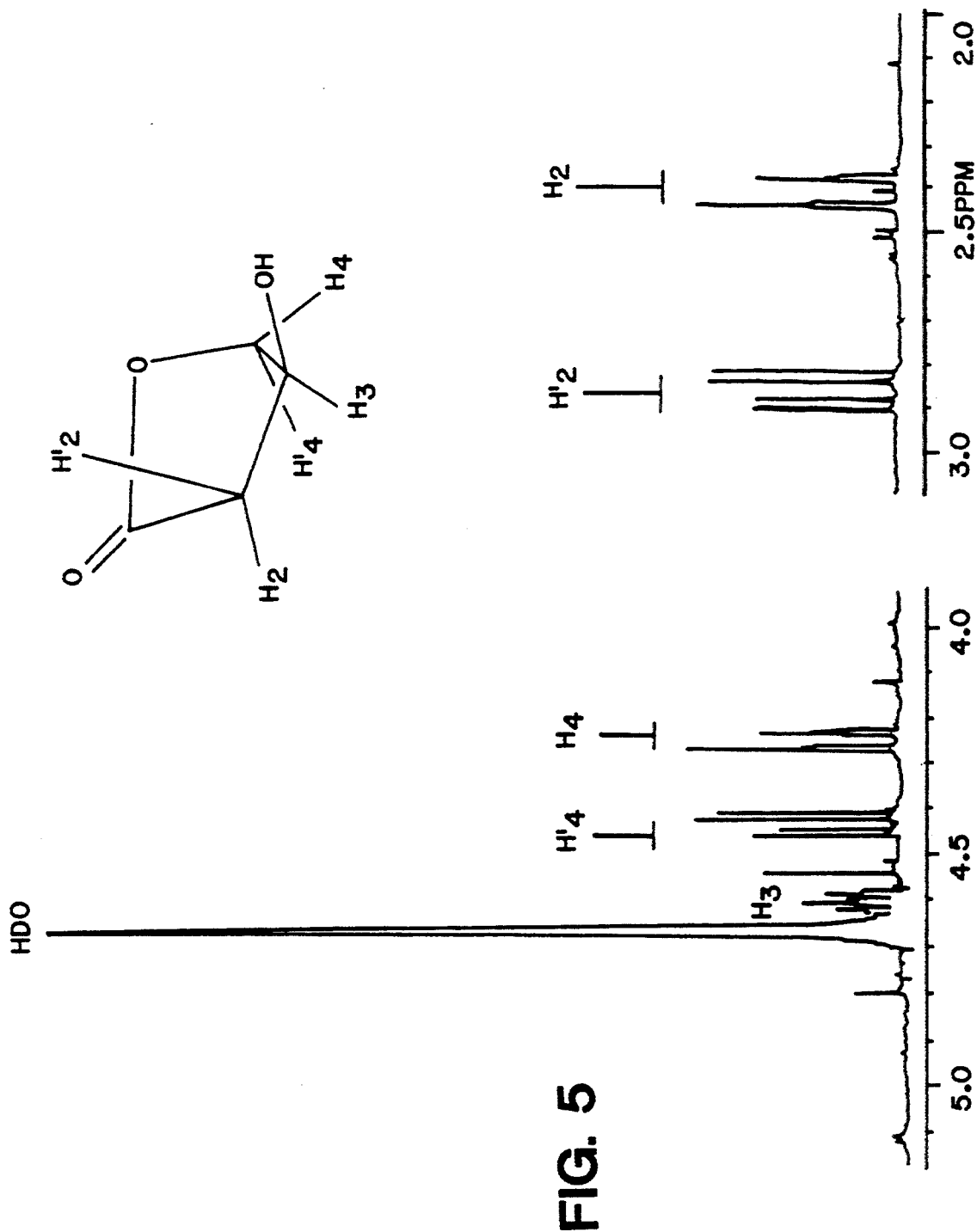

FIG. 5 shows 300 MHz $^1$H-spectrum of (S)-3-hydroxybutyrolactone.

Figure 6:
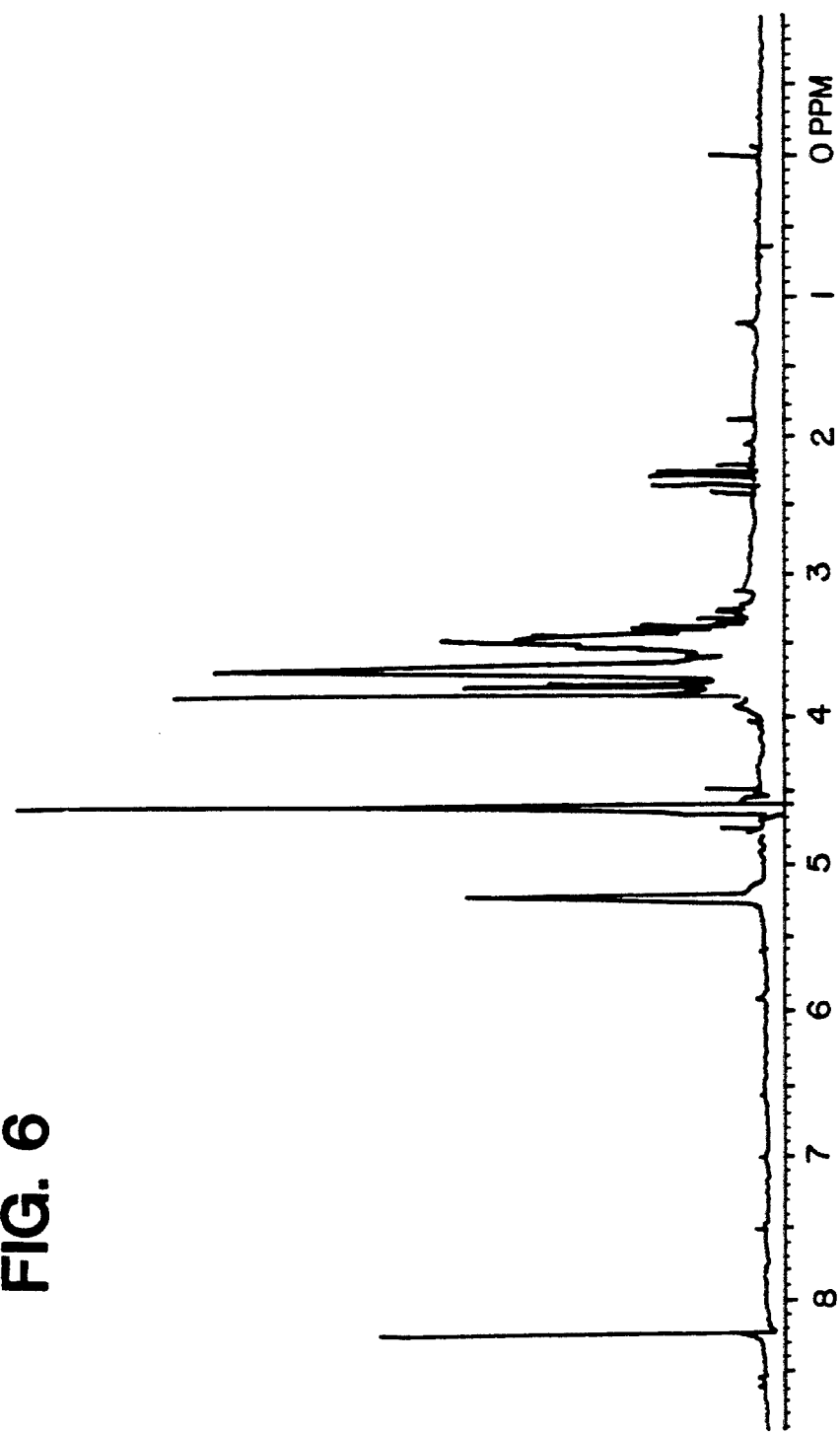

FIG. 6 shows 300 MHz $^1$H-NMR spectrum of crude reaction mixture after treatment of starch with 0.16M sodium hydroxide and 1.3 equivalents of hydrogen peroxide for 24 hours at 70° C. Note the signals between 2 and 2.5 ppm due to the C-2 methylene group of the 3,4-dihydroxybutanoic acid (1).

GENERAL DESCRIPTION

The present invention relates to a process for the conversion of a hexose source containing D-hexose as a substituent and another sugar attached to the D-hexose substituent in the 4 position to 3,4-dihydroxybutyric acid and glycolic acid which comprises: reacting in a reaction mixture the glucose source with a base selected from the group consisting of an alkali metal hydroxide and an alkaline earth metal hydroxide and a peroxide oxidizing agent until 3,4-dihydroxybutyric acid and glycolic acid are formed; and separating the 3,4-dihydroxybutyric acid and glycolic acid from the reaction mixture.

The present invention particularly relates to a process for the conversion of a glucose source containing glucose as a substituent and another sugar attached to the glucose substituent in the 4 position to 3,4-hydroxybutyric acid and glycolic acid which comprises: reacting in a reaction mixture the glucose source with a based selected from the group consisting of an alkali metal hydroxide and an alkaline earth metal hydroxide and hydrogen peroxide until 3,4-dihydroxybutyric acid and glycolic acid are formed; and separating the polypeptide from the reaction mixture. The preferred glucose source is starch or maltose.

The hexoses in the hexose source can be any D-hexose such as galactose, mannose, glucose and the like. These sugars will produce the 3,4-dihydroxybutyric acid by the process of the present invention. The reaction can also be applied to cellulose. Both cellulose and starch are among the most abundant materials on earth. The process of the present invention transforms these and similar abundant, renewable resources to otherwise inaccessible intermediates which can be used in the pharmaceutical, chemical and polymer industries and reduce our dependence on petrochemicals.

The peroxide oxidizing agent can be any peroxide which will produce the 3,4-dihydroxybutyric acid. These include alkaline earth metal peroxides such as barium peroxide, the alkali metal peroxides such as sodium peroxide and hydrogen peroxide. The selection of the peroxide is within the skill of the art.

The base is selected from alkali metal and alkaline earth metal peroxides. These include zinc hydroxide, calcium hydroxide (lime), potassium hydroxide, sodium hydroxide and the like. The selection of the base is with the skill of the art.

Preferably the sodium hydroxide or potassium hydroxide and the hydrogen peroxide molar concentration is between 1 to 2 fold of the total 4-linked hexose. The concentration up to 4 fold can be used but with increasing degradation of the desired product. The D-hexose source is preferably at least about 0.05 percent up to about 80% by weight per volume of the reaction mixture. Preferably the reaction of the base with the glucose source is conducted for at least about 4 hours, preferably between about 14 and 24 hours. The reaction is conducted at a prefer-red temperature between about 25° and 80° C.

The preferred reactions are shown in Schemes I, II and III as follows:

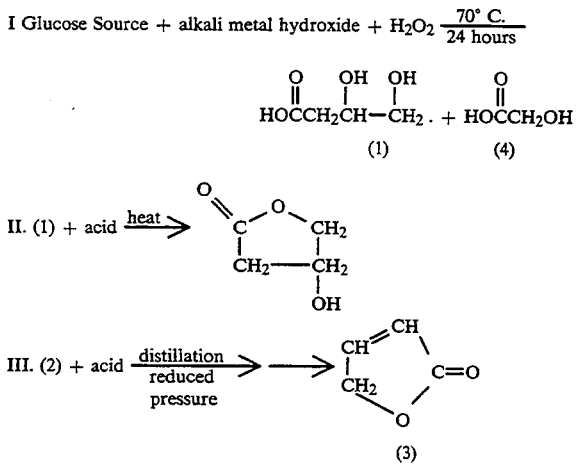

Scission of the bond between the two carboxyl groups of the diulose F resulting from the degradation of the glucose source occurs in the presence of alkaline hydrogen peroxide before any competing reactions to yield the required (1) which is stable to further reaction. On acidification of the reaction mixture, (1) undergoes spontaneous cyclization to yield the gamma-lactone (2) which is dehydrated, on heating in the presence of acid, to yield the unsaturated lactone (3). Treatment of the lactone (2) with hydrogen bromide in acetic acid in the presence of ethanol should readily yield (S)-4-bromo-3-hydroxybutanoic acid ethyl ester, the key fragment in our chiral 3-hydroxy fatty acid syntheses.

(S)-3,4-dihydroxybutanoic acid (1) and glycolic (4) acid were the only products formed from the 4-substituted glycosyl residues of maltose or starch when these compounds were treated with alkaline hydrogen peroxide at 70° C. for 24 hours. Acidification of the reaction mixture and concentration to dryness led to complete conversion of the hydroxybutanoic acid to the gamma-lactone (2). This could be isolated by chromatography on silica gel or converted to the 2(5H)-furanone (3) by distillation of the acidic reaction mixture under reduced pressure. The reaction of maltose or starch under these conditions is thought to proceed by cleavage between the two carbonyl groups of an intermediate 4-deoxy-D-glycerohex-2,3-diulose (F) as in FIG. 1. In the absence of hydrogen peroxide, a complex reaction mixture is formed in which the desired products do not predominate. This reaction opens the way to the preparation, in high yield, of large quantities of valuable chiral building blocks from a cheap, renewable, natural resource.

SPECIFIC DESCRIPTION

Materials and Methods

NMR spectra were recorded on a Varian GEMINI spectrometer operating at 300 MHz for proton frequencies. Chemical shifts are given relative to external TMS. IR spectra were recorded on a NICOLET 710 spectrometer in chloroform solution.

EXAMPLE 1

(S)-3,4-dihydroxybutanoic acid (1): Maltose monohydrate (0.10 g, 0.28 mmoles) was dissolved in 0.16M sodium hydroxide solution (5 ml, 0.8 mmoles) and 30% hydrogen peroxide (40 1, 0.37 mmoles) was added. The mixture was heated at 70° C. for 24 hours to produce (S)-3,4-dihydroxybutanoic acid and glycolic acid in the reaction mixture which can be separated by liquid chromatographic techniques if necessary or desired.

When the reaction was repeated using the same reagents in the same proportions but adding 1.3 molar equivalents of hydrogen peroxide, there was no darkening of the reaction mixture. $^1$H-NMR analysis indicated that the only species giving rise to signals in the region from 0 to 3 ppm was (S)-3,4-dihydroxybutanoic acid. Analysis of the reaction mixture by $^{13}$C-NMR indicated that the reaction was not complete as evidenced by signals still remaining for the anomeric carbon of a glycosidically-linked glucose residue. When the base concentration was increased to 0.16M however, the reaction went to completion (although slight decolorization was noticed) and the signals for the required compound (1) and glycolic acid dominated the $^1$H and $^{13}$C spectra (FIGS. 3 and 4, respectively). The signals for (1) in the $^1$H-NMR spectrum were readily assignable. A doublet of doublets (J=15 Hz and 8.6 Hz) at 2.29 ppm was assigned to one C-2 proton and the other C-2 proton was also a doublet of doublets (J=15 Hz and 4.8 Hz) at 2.38 ppm. A similar pair of doublet of doublets appeared between 3.3 and 3.6 ppm. These were assigned to the protons on C-4. The double of doublets at 3.52 ppm (J=15.8 Hz and 4.1 Hz) was assigned to the proton on C-4 which is anti to the C-3 OH group and the other C-4 proton appeared as a doublet of doublets (J=15.8 Hz and 8.6 Hz) at 3.42 ppm. A multiplet at 3.39 ppm was assigned to H-3. The $^{13}$C spectrum was also quite definitive. The methylene carbon adjacent to the carbonyl carbon appeared at 45.2 ppm. This was the only resonance upfield of 60 ppm (FIG. 4).

EXAMPLE 2

Gamma-lactone (2)—The pH of the reaction mixture of Example 1 adjusted to pH 3.0 with concentrated HCl and was then concentrated to dryness. The residue was dissolved in the minimum volume of methanol and applied to a Silica column packed in chloroform/methanol (9:1) and eluted with chloroform to yield 23.7 mg (85% yield) of the gamma-lactone (2) as a pale yellow syrup. $^1$H-NMR: δ 2.28 (dd, 1H, J18.0 and 0.2 Hz), 2.74 (dd, 1H, J18 and 5.9 Hz), 4.13 (dd, 1H, J9.75 and 0.2 Hz), 4.32 (dd, 1H, J9.75 and 4.5 Hz), 4.49 (m, 1H). $\nu_{max}$ (chloroform) 1783, 1737 cm$^{-1}$.

Lactonization of the acid occurred quite smoothly. This was readily apparent from a downfield shift in all of the proton resonances (relative to those observed in the sodium salt). Both methylene groups still appeared as pairs of mutually-coupled doublet of doublets (FIG. 5). The five-membered ring was not conformationally mobile and was locked in one envelope conformation. The coupling constant of close to 0 Hz between H-3 and one of the C-4 protons (indicating at 90° dihedral angle between two) indicated the conformation shown in FIG. 5. It was evident from the IR spectrum that the gamma-lactone was formed since the carbonyl stretch appeared at its characteristic position of 1782 cm$^{-1}$. It was also evident from the NMR spectra that no racemization of the 3-position had occurred. This possibility is also precluded by the mechanism for the formation of the product.

EXAMPLE 3

(S)-3,4-dihydroxybutanoic acid sodium salt: The lactone (2) was dissolved in methanol (2 ml) and a stoichiometric amount of 0.1M sodium hydroxide (equivalent) was added. The mixture was then concentrated to dryness, $^1$H-NMR: δ 2.27 (dd, 1H, J15.0 and 8.6 Hz), 2.39 (dd, 1H, J15.0 and 4.8 Hz), 3.41 (dd, 1H, J15.8 and 7.9 Hz) 3.51 (dd, 1H, J15.8 and 4.1 Hz), 3.99 (m, 1H).

EXAMPLE 4

2(5H)-furanone (3): The lactone (2) was prepared from 80 g of maltose monohydrate as described before except that all of the reagents were scaled up by a factor of 800. However, after acidification and concentration of the crude mixture, it was subjected to distillation under reduced pressure to yield a light straw colored liquid (3) boiling at 60° C. (25 mm Hg) which contained glycolic acid and water. A later fraction was collected at a bath temperature of 160° C. which was redistilled to give 14.2 g (76%) of the unsaturated lactone (3). $^1$H-NMR: δ 4.88 (t, 2H, 1.5 Hz), 6.13 (at, 1H, 6 and 1.5 Hz), 7.56 (dt, 1H, 6 and 1.5 Hz). $\nu_{max}$ (chloroform) 1779, 1747, 3022 cm$^{-1}$.

No attempt was made to optimize conditions for the dehydration of (2) to yield the unsaturated lactone (3). However, the degree of conversion was quite high. The crude 2(5H)-furanone (3) was obtained by a simple bulb-to-bulb distillation of the acidified reaction mixture and NMR analysis indicated that it was the only component besides about 15% of the saturated hydroxylactone (2). The product (3) was readily purified by another distillation to yield the pure unsaturated furanone (3) in 76% yield.

COMPARATIVE EXAMPLE 5

Oxidation of Starch: Soluble starch (0.10 g) was dissolved in 0.16M sodium hydroxide (5 ml) and the solution heated at 70° C. for 48 hours. The reaction mixture was concentrated to dryness and analyzed directly by $^1$H-NMR spectroscopy. Treatment of maltose with 0.16M sodium hydroxide in the absence of hydrogen peroxide for 24 hours led to the formation of a black complex mixture. This discolorization was evident after only 15 minutes. The $^1$H-NMR spectrum of the crude reaction mixture was quite complex and there were several resonances between 0 and 3 ppm (FIG. 2). These were attributed to methylene and methyl groups from 2,4-dihydroxybutanoic acid, acetylacetone, acetate and other degradation products. A pair of mutually-coupled doublet of doublets centered at 2.34 ppm was assigned to the methylene protons of (S)3,4-dihydroxybutanoic acid (4).

EXAMPLE 6

Application of the alkaline peroxide oxidation to soluble starch in the manner of Example 1 over a period of 48 hours gave good conversion to the dihydroxy butanoic acid (1) and glycolic acid (4). $^1$H-NMR spectroscopy (FIG. 6) clearly demonstrated that these were the only products formed.

COMPARATIVE EXAMPLE 7

The same reaction conditions with the exclusion of hydrogen peroxide again gave a complex series of signals between 0 and 3 ppm as in Example 5. The reaction on starch was not complete after 48 hours but prehydrolysis in 0.5M HCl at 100° C. for 20 minutes followed by the same treatment gave better transformation.

The rate of the reaction with starch is proportional to the concentration of reducing-end sugars. Starch, because of its high molecular weight has a lower rate than maltose. The effective concentration could be increased by pre-hydrolyzing the starch to give smaller units. Since the product is generated by peeling along the starch molecule from the reducing end to the non-reducing end and liberating a new reducing end in each cycle and since none of the required product can be produced from the non-reducing end, there is a compromise between reaction rate and overall yield which must be kept in mind during the prehydrolysis. If the yield is quantitative and the chain length is infinite, the maximum mass conversion obtainable is about 74%. In other words, 100 g of starch will yield 74 g of the dihydroxy butanoic acid. However, the rate of reaction will be extremely slow. If the polymer is pre-hydrolyzed to oligomers with an average chain length of 10 glucose units, the yield will be 66 g of product from 100 g of material or 66% yield. This is not a much lower yield and the reaction is complete in a very short time.

It is intended that the foregoing description be only illustrative of the present invention and that the present invention be limited only by the hereinafter appended claims.

I claim:

1. A process for the conversion of a hexose source containing hexose as a substituent and another sugar attached to the hexose substituent in the 4 position to a 3,4-dihydroxybutanoic salt which comprises:

(a) reacting in a reaction mixture consisting essentially of the hexose source with a base selected from the group consisting of an alkali metal hydroxide and an alkaline earth metal hydroxide and hydrogen peroxide until 3,4-dihydroxybutyric acid and glycolic acid are formed;

(b) acidifying the reaction mixture to convert the 3,4-dihydroxybutyric acid to an internal cyclic ester; and (c) heating the internal cyclic ester with a second base selected from the group consisting of an alkali metal hydroxide and an alkaline earth metal hydroxide to produce the 3,4-dihydroxybutanoic salt.

2. The process of claim 1 wherein the internal ester is a lactone.

3. The process of claim 1 wherein the ester is removed from the reaction mixture by distillation.

4. The process of claim 1 wherein the reaction mixture is acidified and heated to convert the (S)-3,4-dihydroxybutanoic acid to (S)-3,4-dihydroxybutanoic acid gamma-lactone.

5. The process of claim 1 wherein the hexose source is a glucose source.

6. The process of claim 1 wherein the hexose source is selected from the group consisting of maltose, lactose, maltodextran, starch, starch hydrolysate and cellulose.

7. The process of claim 1 wherein the peroxide and the base in step (a) are present in a range up to a 4 molar excess over the hexose and wherein the hexose is between about 0.05 to 80% by weight of the reaction mixture.

8. The process of claim 7 wherein the base is between about 0.005M and 0.2M and wherein hydrogen peroxide is between about 0.05M and 0.2M.

9. The process of claim 8 wherein the hexose source is glucose.

10. The process of claim 9 wherein the reaction in step (a) is conducted at about 25° to 80° C. for at least about 4 hours.

11. The process of claim 10 wherein the reaction is conducted at about 70° C. for between about 14 and 24 hours.

12. The process of claim 1 wherein the internal cyclic ester is separated from the reaction mixture in step (b).

13. The process of claim 11 wherein the base in step (a) and step (c) is sodium hydroxide.

14. A process for preparing a 3,4-dihydroxybutanoic salt which comprises:

(a) reacting 3,4-dihydroxybutyric acid with an acid to form an internal cyclic ester; and (b) heating the internal cyclic ester with a second base selected from the group consisting of an alkali metal hydroxide and an alkaline earth metal hydroxide to produce the 3,4-dihydroxybutanoic salt.

* * * * *